United States Patent [19]
Suzuki et al.

[11] Patent Number: 6,025,520
[45] Date of Patent: *Feb. 15, 2000

[54] METHOD FOR PREPARING (METH) ACRYLIC ACID ESTER

[75] Inventors: Yoshiro Suzuki; Masahiko Yamagishi; Chikara Sugimoto; Norioki Mine, all of Yokkaichi, Japan

[73] Assignee: Mitsubishi Chemical Corporation, Tokyo, Japan

[ * ] Notice: This patent is subject to a terminal disclaimer.

[21] Appl. No.: 09/192,319

[22] Filed: Nov. 16, 1998

Related U.S. Application Data

[62] Division of application No. 08/910,670, Aug. 13, 1997, Pat. No. 5,866,713.

[30] Foreign Application Priority Data

Aug. 20, 1996 [JP] Japan ................................... 8-218627

[51] Int. Cl.$^7$ .................................................. C07C 69/52
[52] U.S. Cl. ............................................................ 560/205
[58] Field of Search ............................................. 560/205

[56] References Cited

U.S. PATENT DOCUMENTS

| | | | |
|---|---|---|---|
| 4,250,328 | 2/1981 | Fujita et al. | 560/205 |
| 4,435,594 | 3/1984 | Matsumura et al. | 560/205 |

FOREIGN PATENT DOCUMENTS 1 387 704   3/1975   United Kingdom .

*Primary Examiner*—Paul J. Killos
*Assistant Examiner*—J. Parsa
*Attorney, Agent, or Firm*—Oblon, Spivak, McClelland, Maier & Neustadt, P.C.

[57] ABSTRACT

A method for preparing a (meth)acrylic acid ester, which comprises reacting (meth)acrylic acid with a $C_{1-3}$ alcohol in the presence of a strongly acidic ion exchange resin as a catalyst, wherein the reaction is carried out under reduced pressure while the molar ratio of the alcohol to the (meth) acrylic acid is adjusted to be less than 1, whereby it is possible not only to improve the esterification yield by one pass but also to reduce the amount of a by-product alkoxypropionate which is problematic in the purification system.

11 Claims, 1 Drawing Sheet

METHOD FOR PREPARING (METH) ACRYLIC ACID ESTER

This application is a division of 08/910,670 filed on Aug. 13, 1997, U.S. Pat. No. 5,866,713.

BACKGROUND OF THE INVENTION

1. Field of the Invention

The present invention relates to a method for preparing a (meth)acrylic acid ester. Particularly, the present invention relates to a method for preparing a (meth)acrylic acid ester by reacting (meth)acrylic acid with a $C_{1-3}$ alcohol under specific conditions. Here, the term "(meth)acrylic" means each of "acrylic" and "methacrylic".

2. Discussion of Background

A (meth)acrylic acid ester is industrially important as a material for synthetic fibers, coating materials, adhesives, etc.

It is well known to use an ion exchange resin as a catalyst for the preparation of a (meth)acrylic acid ester by reacting (meth)acrylic acid with an alcohol. This reaction is an equilibrium reaction, and it is accordingly common to use one of the reactants, usually the alcohol, in excess in the reaction and to remove water formed by the reaction from the reaction system, to shift the equilibrium to increase the conversion.

As a method for removing water, various proposals have heretofore been made, such as a high temperature reaction, a reduced pressure reaction and a method by means of azeotropic distillation.

For example, JP-A-8-143512 proposes a method for preparing a (meth)acrylic acid ester by an esterification reaction of (meth)acrylic acid with a $C_{1-8}$ alcohol in the presence of an ion exchange resin as a catalyst, wherein the reaction is carried out under reduced pressure, while the reaction liquid is circulated with heating to remove formed water whereby a high conversion is attained. However, this method has a drawback that the reaction liquid must be heated and circulated in order to attain the high conversion, and working Examples are limited to cases of higher alcohols having 4 or 6 carbon atoms.

JP-A-53-56611 proposes a method for preparing an acrylic acid ester by reacting acrylic acid with a higher alcohol in the presence of an ion exchange resin as a catalyst, wherein the reaction is carried out under reduced pressure using the alcohol in excess. In this case, it is disclosed that by carrying out the reaction under reduced pressure, a high conversion can be accomplished by one pass without using a solvent, the selectivity for the reaction is good as compared with reactions under atmospheric pressure, and the increase of by-products is slow. However, the reaction is carried out under a condition that the alcohol is in excess, whereby the proportion in formation of an alkoxypropionic acid and an alkoxypropionic acid ester is deviated to the alkoxypropionic acid ester. Accordingly, this method has a drawback that when the reaction is carried out by using a lower alcohol such as methanol, the alkoxypropionic acid ester will be distilled together with the acrylic acid ester in the purification system and tends to be accumulated in the purification system, whereby the load in the purification process tends to be large.

Further, JP-A-55-122740 proposes a method for preparing a (meth)acrylic acid ester by reacting (meth)acrylic acid with methanol or ethanol in the presence of an ion exchange resin as a catalyst, wherein the reaction is carried out by maintaining the reaction system in a gas-liquid mixed state while supplying the feed material to the reactor. In this case, for esterification of a lower alcohol, the reaction is not required to be carried out under reduced pressure, and it is disclosed that a high conversion can be accomplished by one pass by maintaining the gas-liquid mixed phase under atmospheric pressure. However, according to the study conducted by the present inventors, it was impossible to accomplish a conversion beyond a level equal to a liquid phase reaction even at a temperature at which a gas-liquid mixed phase is obtained under atmospheric pressure in the reaction of a lower alcohol. Further, this method has a drawback that the reaction temperature tends to be somewhat high in order to attain the gas-liquid mixed phase under atmospheric pressure, and thus it is likely to lead to a trouble that (meth)acrylic acid undergoes polymerization.

As described above, in a conventional esterification method which is carried-out in the presence of an excess amount of an alcohol, the conversion in the esterification reaction has not necessarily been adequate, and there has been a problem that the amount of resulting by-product such as an alkoxypropionic acid ester which will be problematic in the purification system or a polymer of an acrylic acid ester, is substantial.

Thus, it is an object of the present invention to provide a method whereby in the preparation of a (meth)acrylic acid ester by reacting (meth)acrylic acid with a $C_{1-3}$ lower alcohol in the presence of an ion exchange resin as a catalyst, it is possible not only to improve the esterification yield by one pass but also to reduce as far as possible the amount of formation of a by-product which will be problematic in the purification system.

SUMMARY OF THE INVENTION

The present inventors have conducted extensive studies to solve the above problems and as a result, have found that by carrying out the reaction under reduced pressure in the presence of a strongly acidic ion exchange resin as a catalyst and further adjusting the molar ratio of the lower alcohol to the (meth)acrylic acid to be less than 1, it is possible not only to improve the conversion and selectivity for the esterification reaction by one pass but also to reduce, particularly in the reaction of acrylic acid with methanol, the amount of formation of methyl methoxypropionate which has a boiling point close to acrylic acid and thus is problematic in the purification system. The present invention has been accomplished on the basis of this discovery.

Namely, the present invention provides:

1. A method for preparing a (meth)acrylic acid ester, which comprises reacting (meth)acrylic acid with a $C_{1-3}$ alcohol in the presence of a strongly acidic ion exchange resin as a catalyst, wherein the reaction is carried out under reduced pressure while the molar ratio of the alcohol to the (meth)acrylic acid is adjusted to be less than 1.
2. The method according to Item 1, wherein methanol is used as the $C_{1-3}$ alcohol.
3. The method according to Item 1 or 2, wherein the molar ratio of the alcohol to the (meth)acrylic acid is from 0.3 to less than 1.
4. The method according to any one of Items 1 to 3, wherein the reaction pressure is from 100 to 500 Torr.
5. The method according to any one of Items 1 to 4, wherein the reaction temperature is from 60 to 130° C.
6. The method according to any one of Items 1 to 5, herein a fixed bed reactor is used as the reactor and the space velocity ($hr^{-1}$) of the reaction liquid fed to the fixed bed reactor is from 0.1 to less than 1.

7. A method for preparing methyl (meth)acrylate which comprises reacting (meth)acrylic acid with methanol in the presence of a strongly acidic ion exchange resin as a catalyst, wherein the reaction is carried out under a pressure of from 100 to 500 Torr at a temperature of from 60 to 130° C. at a space velocity ($hr^{-1}$) of from 0.1 to less than 1, while the molar ratio of methanol to the (meth) acrylic acid is adjusted to be from 0.3 to less than 1.

8. The method according to any one of Items 1 to 7, wherein (meth)acrylic acid and methanol are reacted by supplying them to a fixed bed reactor packed with the strongly acidic ion exchange resin, wherein the (meth)acrylic acid and the methanol are contacted in the gas-liquid parallel flow mode.

9. The method according to any one of Items 1 to 8, wherein a reaction mixture obtained by the reaction of (meth) acrylic acid with the alcohol under reduced pressure, is supplied to a (meth)acrylic acid separation distillation column of a next step without cooling or condensing it.

10. The method according to any one of Items 1 to 9, wherein when a reaction mixture obtained by the reaction of (meth)acrylic acid with the alcohol under reduced pressure is fed to a (meth)acrylic acid separation distillation column of a next step, a liquid component and a gas component of the reaction mixture are separated, and the gas component is supplied in the vicinity of the top of the distillation column, and the liquid component is supplied to a position lower than the supplying position of the gas component.

11. The method according to any one of Items 1 to 10, wherein a heat exchanger type multitubular reactor is used as an esterification reactor, wherein the catalyst is packed in the reaction tubes, and the outside of the reaction tube is heated by steam or a heating medium.

12. The method according to any one of Items 1 to 11, wherein acrylic acid is used as the (meth)acrylic acid.

DETAILED DESCRIPTION OF THE PREFERRED EMBODIMENTS

Figure 1:
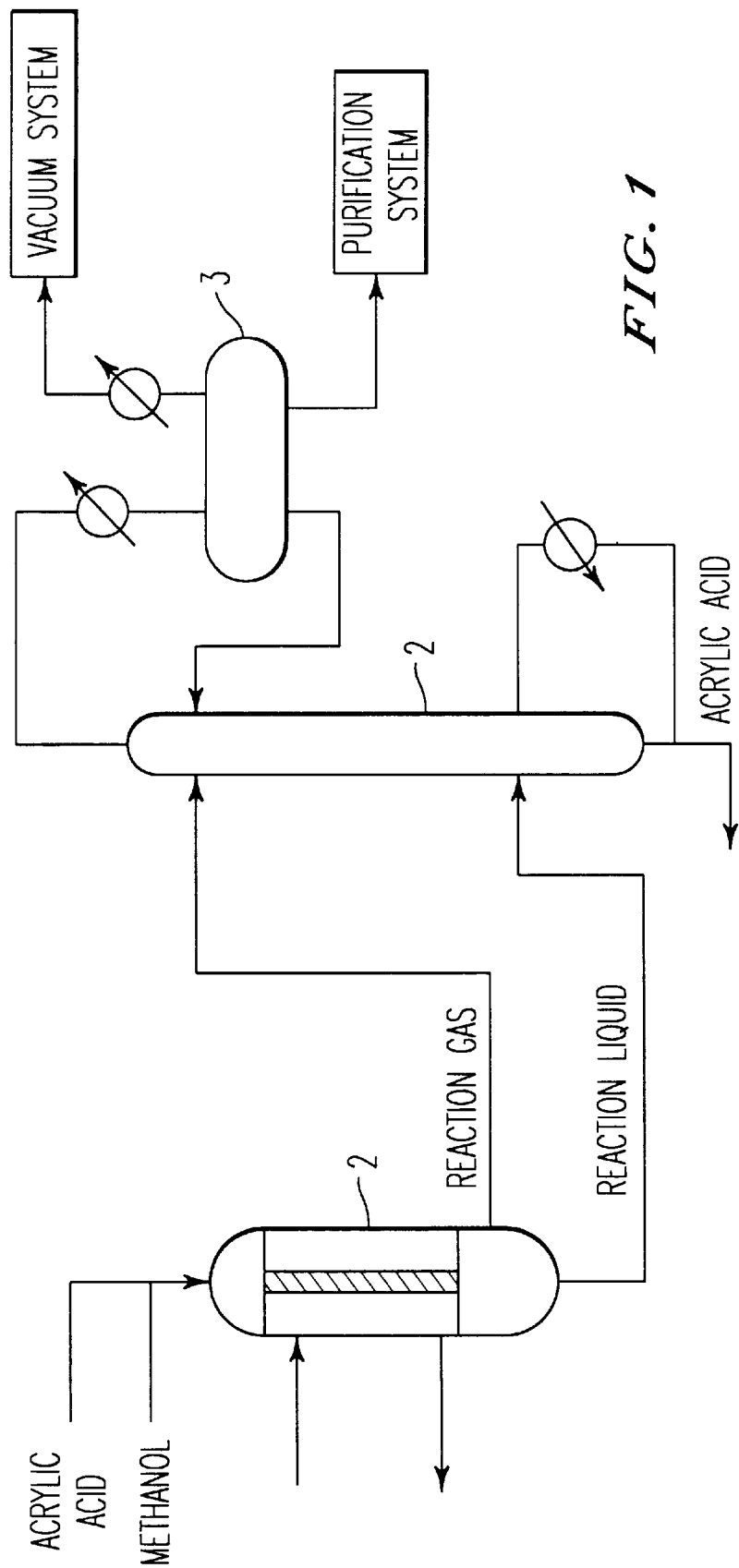
FIG. 1 is a flow sheet illustrating an embodiment of the present invention, wherein reference numeral 1 indicates an esterification reactor, numeral 2 indicates an acrylic acid separating column and numeral 3 indicates a condenser.

Now, the method of the present invention will be described in detail with reference to the preferred embodiments.

The $C_{1-3}$ alcohol to be used in the present invention may, for example, be methanol, ethanol, n-propanol or i-propanol. The alcohol may be of a purity useful for an industrial purpose. However, the water content should preferably be as small as possible.

When methanol is employed as the alcohol, in a case of a conventional method wherein esterification is carried out in the presence of an excess amount of methanol, the boiling point (143° C.) of methyl methoxypropionate formed as a by-product is very close to the boiling point (141° C.) of acrylic acid and thus will be problematic in its separation in the purification system. Whereas, in the present invention, the esterification is carried out in the presence of an excess amount of acrylic acid, whereby the amount of the formation of the by-product can be reduced to a large extent.

The acrylic acid or methacrylic acid to be used in the present invention may be of a purity useful for an industrial purpose. However, the water content should preferably be small as possible.

The molar ratio of the lower alcohol to the (meth)acrylic acid is usually from 0.3 to less than 1, preferably from 0.5 to 0.75. Any remaining (meth)acrylic acid will be recovered in a purification step and returned to the reactor.

The strongly acidic cation exchange resin to be used in the present invention is usually the one obtained by treating a styrene-divinyl benzene copolymer with sulfuric acid. As the resin, a porous or gel type resin may be employed. However, a porous type resin is preferably employed. Especially when crude acrylic acid is to be used, it is preferred to use a porous type resin excellent in organic stain resistance. As a porous strongly acidic cation exchange resin, the one having a crosslinking degree of from 2 to 16%, a porosity of from 0.1 to 1.0 ml/g and an average pore size of from 100 to 600 Å is preferred. Specific examples include Diaion PK-208, PK-216 and P-228 (manufactured by Mitsubishi Chemical Corporation), HCR-W2-H, MSC-1 and 88 (manufactured by Dow Chemical Company), Duolite C-260 and Amberlyst-16 (manufactured by Rohm & Haas Co.), and SPC-108, SPC-112 (manufactured by Bayer).

Among them, Diaion PK-216 (manufactured by Mitsubishi Chemical Corporation) or HCR-W2-H (manufactured by Dow Chemical Company) is preferably employed.

As a reactor to be used for the preparation of a (meth) acrylic acid ester employing such an ion exchange resin as a catalyst, is preferably a fixed bed reactor, and as its reaction system, it is preferred to employ a system wherein the reaction is carried out as a gas-liquid-solid three phase reaction. In the present invention, the gas-liquid flow mode is preferably a gas-liquid parallel flow.

In a case where the reaction is carried out in a gas-liquid counter flow, it is necessary to secure the flow of gas by adjusting the shape, size and packing mode of the strongly acidic ion exchange resin.

Further, as a preliminary stage for the gas-liquid-solid three phase reaction, an esterification reaction in a fixed bed under atmospheric pressure or elevated pressure may be combined.

The reaction temperature is usually from 60 to 130° C., preferably from 60 to 100° C., more preferably from 70 to 90° C. If the temperature is lower than 60° C., the activities of the catalyst tend to be inadequate, and the reaction rate tends to be low, whereby the volume of the reactor will have to be increased, such being not economical. Further, since the boiling point of acrylic acid under a pressure of 500 Torr is 129° C., and if the temperature exceeds 130° C., acrylic acid tends to evaporate under reduced pressure, whereby the effects of the present invention will be low.

The pressure for the reaction is preferably from 100 to 500 Torr, more preferably from 200 to 300 Torr. If the pressure is lower than 100 Torr, acrylic acid is likely to evaporate, whereby the effects of the present invention will be low.

The space velocity ($hr^{-1}$) of the reaction liquid to be supplied to the fixed bed reactor is usually from 0.1 to less than 1.0, preferably from 0.33 to 0.5. If the space velocity (SV) is less than 0.1, the productivity per unit volume of the reactor tends to low, such being uneconomical. Further, if SV is 1.0 or higher, no adequate conversion tends to be obtained.

To conduct the reaction under reduced pressure at a temperature of from 60 to 130° C., it is preferred to employ a heat exchanger-type multitubular reactor as the esterification reactor. This reactor is disposed vertically and the ion exchange resin as a catalyst is packed in the reaction tubes. Then, preferably, liquid reactants comprising (meth)acrylic acid and the alcohol as the main components, are supplied from an upper portion. Steam or a heating medium is supplied to the outside of the reaction tubes to maintain the reaction temperature in the reaction tubes. The pressure for the reaction can be maintained from 100 to 500 Torr by connecting the outlet of the esterification reactor to a vacuum system such as a vacuum pump via a condenser.

As shown in JP-A-2-279655, the reaction mixture after the esterification reaction is led to a (meth)acrylic acid separation step as a next step, whereby unreacted (meth) acrylic acid will be separated.

The separation of (meth)acrylic acid is usually carried out by distillation. However, it is not desirable to expose (meth) acrylic acid to a high temperature from the viewpoint of preventing from polymerization. Accordingly, it is preferred to operate the (meth)acrylic acid separation distillation column under reduced pressure. Preferably, the outlet of the esterification reactor is connected to the acrylic acid separation distillation column, so that the reaction mixture is directly supplied to the acrylic acid separation distillation column, whereby the reaction system and the distillation system can be maintained under reduced pressure consistently.

In the present invention, the esterification reactor is preferably maintained under a reduced pressure of from 100 to 500 Torr, and the temperature is maintained at a level of from 60 to 130° C., by heating with steam or a heating medium. Under such reaction conditions, a part of the reaction liquid evaporates as the esterification reaction proceeds. The reaction mixture at the outlet of the esterification reactor is in a gas-liquid mixed state wherein the reaction liquid and the gas formed by evaporation of a part thereof, are co-existing. In a step next to the esterification reaction, (meth)acrylic acid is separated by distillation in the (meth) acrylic acid separation distillation column. Here, by supplying the reaction mixture from the outlet of the esterification reactor to the (meth)acrylic acid separation distillation column without condensing or cooling it, it is possible to effectively utilize the heat energy supplied to the esterification reactor. Thus, it has been found that separation of (meth)acrylic acid can be carried out more effectively from the viewpoint of the energy and separation by distillation.

Further, the present inventors have confirmed that of the reaction of the mixture at the reactor in the gas-liquid coexistent state, the liquid component contains (meth) acrylic acid as the main component, and the gas component is a mixture containing the alcohol, the (meth)acrylic acid ester and water formed by the esterification reaction, as the main component. These compositions vary depending upon the type of the alcohol, the reaction temperature and the reaction pressure. However, the higher the reaction pressure and the lower the reaction temperature, the smaller the inclusion of (meth)acrylic acid in the gas component at the outlet of the reactor. In a reverse case, the content of low boiling components such as a (meth)acrylic acid ester in the liquid component tends to be small.

It has been found that when the reaction mixture at the outlet of the reactor is supplied to the (meth)acrylic acid separation distillation column, the liquid component containing (meth)acrylic acid as the main component and the gas component containing the alcohol and the (meth)acrylic acid ester as the main components, are preliminarily separated, and this gas component is fed in the vicinity of the top of the (meth)acrylic acid separation distillation column and the liquid component is fed at a position lower than the supplying position of the above gas component to the distillation column.

Now, the present invention will be described in detail with reference to the flow sheet. (Meth)acrylic acid and the alcohol are mixed and supplied from an upper portion of an esterification reactor 1. In the interior of the esterification reactor, an ion exchange resin is packed as a catalyst. To the esterification reactor, steam or a heating medium is supplied to maintain the reaction temperature.

A reaction mixture withdrawn from the esterification reactor 1 is separated into a liquid component and a gas component. Preferably, the gas component is supplied at an upper portion of a (meth)acrylic acid separation column 2 i.e. in the vicinity of the top of the distillation column. This (meth)acrylic acid separation column 2 is connected to a vacuum system via a condenser 3. From the top of the (meth)acrylic acid separation column 2, a mixture comprising the alcohol, the (meth)acrylic acid ester and the water formed by the reaction, is distilled, and in the next step, the alcohol and water are separated from this mixed liquid to obtain the (meth)acrylic acid ester as a product. From the bottom of the column, substantially (meth)acrylic acid flows out, and the (meth)acrylic acid is, after separating the reaction by-product (not shown in the flow sheet) or as it is, recycled for use again in the esterification reaction.

Now, the present invention will be described in further detail with reference to Examples and Comparative Examples. However, it should be understood that the present invention is by no means restricted to such specific Examples.

EXAMPLE 1

100 cc of a strongly acidic ion exchange resin (PK-216) was packed and fixed in an inner pipe of a jacketed pipe reaction column made of glass having an inner diameter of 20 mm and a length of 500 mm, and a temperature sensor terminal was inserted at the center portion of this reaction column. To the outer jacket, a heating medium (triethylene glycol) heated to 80° C. by a mantle heater, was circulated. The pressure of the reaction system was maintained at 300 Torr (0.04 MPa).

As the feed material, an acrylic acid/methanol mixed liquid wherein the molar ratio of methanol to acrylic acid was 0.75, was used. To this mixed liquid, 1,000 ppm of hydroquinone, 500 ppm of hydroquinone monomethyl ether and 500 ppm of phenothiazine were added as polymerization-inhibitors.

The mixed feed material was supplied at SV=0.33 from the upper portion of the reactor via a back-pressure valve, by a constant delivery pump.

The reaction liquid obtained from the lower portion of the reaction column was completely condensed to obtain an esterification product comprising 15.92 mol % of acrylic acid (hereinafter referred to simply as AA), 2.05 mol % of methanol (hereinafter referred to simply as MeOH), 40.80 mol % of methyl acrylate (hereinafter referred to simply as AEM), 40.80 mol % of water, 0.24 mol % of methoxypropionic acid (hereinafter referred to simply as MPA), and 0.19 mol % of methyl methoxypropionate (hereinafter referred to simply as MPM). The conversion of methanol was as high as 95.32% (the equilibrium conversion from calculation: 83%). The selectivity was 98.50%.

The reaction results under the above conditions are shown in Table 1.

EXAMPLES 2 AND 3 AND COMPARATIVE EXAMPLE 1

The esterification reaction was carried out in the same manner as in Example 1 except that the reaction pressure was changed as identified in Table 1. The results are shown in Table 1.

EXAMPLES 4 TO 6

The reaction was carried out under the same conditions as in Example 1 except that the reaction pressure was changed as shown in Table 2 and the molar ratio (MeOH/AA) was changed to 0.5. The results are shown in Table 2.

EXAMPLE 7 AND COMPARATIVE EXAMPLE 2

Using the same apparatus as used in Example 1, the reaction was carried out at 80° C. under 300 Torr with a molar ratio of 0.85 (Example 7) or 1.4 (Comparative Example 2). The reaction results are shown in Table 3.

EXAMPLE 8 AND COMPARATIVE EXAMPLE 3

The reaction was carried out in the same manner as in Example 1 except that the temperature of the heating medium was changed to 65° C. (Example 8) or 55° C. (Comparative Example 3) as shown in Table 4. The results are shown in Table 4 together with the results of Example 1.

EXAMPLE 9

The reaction was carried out under the same conditions as in Example 1, but the reaction liquid was not completely condensed, and a gas component and a liquid component were separately obtained. The results are shown in Table 5. The gas component flowed out at a rate of 3.12 g/hr and comprised 80.42 mol % of AEM, 5.66 mol % of methanol and 14.15 mol % of water. The liquid component flowed out at a rate of 27.23 g/hr and comprised 42.76 mol % of water, 37.77 mol % of AEM, 17.25 mol % of acrylic acid, 1.76 mol % of methanol, 0.26 mol % of MPA and 0.20 mol % of MPM.

EXAMPLE 10 AND COMPARATIVE EXAMPLE 4

The reaction was carried out in the same manner as in Example 1 except that ethanol (hereinafter referred to simply as EtOH) was used instead of methanol, and the molar ratio (EtOH/AA) and the reaction pressure were changed as identified in Table 6. The results are shown in Table 6.

EXAMPLE 11

The esterification reaction was carried out in the same manner as in Example 1 except that methacrylic acid was used instead of acrylic acid, and the pressure was changed to 200 Torr, and SV was changed to 0.2.

As a result, from the lower portion of the reaction column, an esterification product was obtained which comprised 19.34 mol % of methacrylic acid, 4.04 mol % of methanol, 38.31 mol % of methyl methacrylate and 38.31 ml % of water.

The conversion of methanol by one pass was as high as 90%.

COMPARATIVE EXAMPLE 5

The reaction was carried out in the same manner as in Example 11 except that the reaction pressure was atmospheric pressure, whereby the conversion of methanol was 77%.

It is evident from the above Examples and Comparative Examples that according to the present invention, when a (meth)acrylic acid ester is prepared by reacting (meth) acrylic acid with a $C_{1-3}$ lower alcohol in the presence of an ion exchange resin as the catalyst, it is possible not only to improve the selectivity and conversion by one pass in the esterification reaction but also to substantially reduce the amount of formation of a by-product alkoxypropionic acid ester which will be problematic in the purification system.

TABLE 1

| Example No. | 1 | 2 | 3 | Comparative Example 1 |
|---|---|---|---|---|
| Molar ratio (MeOH/AA) | 0.75 | 0.75 | 0.75 | 0.75 |
| Reaction pressure (Torr) | 300 | 200 | 450 | 760 |
| Reaction temp. (°C.) | 73 | 70 | 77 | — |
| Heating medium temp. (°C.) | 80 | 80 | 80 | 80 |
| SV (hr$^{-1}$) | 0.33 | 0.33 | 0.33 | 0.33 |
| Conversion of methanol (%) | 95.32 | 94.95 | 92.50 | 82.67 |
| Composition (mol %) AEM | 40.80 | 40.15 | 38.65 | 32.94 |
| MPM | 0.19 | 0.19 | 0.43 | 0.53 |
| MPA | 0.24 | 0.24 | 0.55 | 0.36 |
| AEM selectivity (%) | 98.50 | 98.48 | 96.48 | 95.87 |

TABLE 2

| Example No. | 4 | 5 | 6 |
|---|---|---|---|
| Molar ratio (MeOH/AA) | 0.5 | 0.5 | 0.5 |
| Reaction pressure (Torr) | 200 | 300 | 450 |
| Reaction temp. (°C.) | 75 | 75 | 78 |
| Heating medium temp. (°C.) | 80 | 80 | 80 |
| SV (hr$^{-1}$) | 0.33 | 0.33 | 0.33 |
| Conversion of methanol (%) | 97.68 | 95.87 | 93.50 |
| Composition (mol %) AEM | 33.59 | 32.88 | 30.15 |
| MPM | 0.08 | 0.15 | 0.34 |
| MPA | 0.20 | 0.33 | 0.67 |
| AEM selectivity (%) | 98.94 | 98.12 | 95.71 |

TABLE 3

| Example No. | 1 | 5 | 7 | Comparative Example 2 |
|---|---|---|---|---|
| Molar ratio (MeOH/AA) | 0.75 | 0.5 | 0.85 | 1.4 |
| Reaction pressure (Torr) | 300 | 300 | 300 | 300 |
| Reaction temp. (°C.) | 73 | 75 | 73 | — |
| Heating medium temp. (°C.) | 80 | 80 | 80 | 80 |
| SV (hr$^{-1}$) | 0.33 | 0.33 | 0.33 | 0.33 |
| Conversion of methanol (%) | 95.32 | 95.87 | 94.23 | 96.12* |
| Composition (mol %) AEM | 40.80 | 32.88 | 42.30 | 40.43 |
| MPM | 0.19 | 0.15 | 0.28 | 0.31 |
| MPA | 0.24 | 0.33 | 0.16 | 0.01 |
| AEM selectivity (%) | 98.50 | 98.12 | 98.33 | 98.47 |

*Conversion of acrylic acid

TABLE 4

| Example No. | 1 | 8 | Comparative Example 3 |
|---|---|---|---|
| Molar ratio (MeOH/AA) | 0.75 | 0.75 | 0.75 |
| Reaction pressure (Torr) | 300 | 300 | 300 |
| Reaction temp. (°C.) | 73 | — | — |
| Heating medium temp. (°C.) | 80 | 65 | 55 |
| SV (hr$^{-1}$) | 0.33 | 0.33 | 0.33 |

TABLE 4-continued

| Example No. | 1 | 8 | Comparative Example 3 |
|---|---|---|---|
| Conversion of methanol (%) | 95.32 | 85.19 | 77.26 |
| Composition AEM (mol %) | 40.80 | 36.70 | 32.55 |
| MPM | 0.19 | 0.23 | 0.24 |
| MPA | 0.24 | 0.15 | 0.10 |
| AEM selectivity (%) | 98.50 | 98.36 | 98.25 |

TABLE 5

| Example No. | | 9 | |
|---|---|---|---|
| Molar ratio (MeOH/AA) | | 0.75 | |
| Reaction pressure (Torr) | | 300 | |
| Reaction temp. (°C.) | | 73 | |
| Heating medium temp. (°C.) | | 80 | |
| SV (hr$^{-1}$) | | 0.33 | |
| Conversion of methanol (%) | | 95.32 | |
| | | Liquid phase | Gas phase |
| Flow rate (g/hr) | | 27.23 | 3.12 |
| Composition mol (%) | AEM | 37.77 | 80.42 |
| | MeOH | 1.76 | 5.66 |
| | H$_2$O | 42.76 | 14.15 |
| | AA | 17.25 | 0.00 |
| | MPM | 0.20 | 0.00 |
| | MPA | 0.26 | 0.00 |
| AEM selectivity (%) | | 98.50 | |

TABLE 6

| Example No. | 10 | Comparative Example 4 |
|---|---|---|
| Molar ratio (EtOH/AA) | 0.5 | 0.5 |
| Reaction pressure (Torr) | 200 | 760 |
| Reaction temp. (°C.) | — | — |
| Heating medium temp. (°C.) | 80 | 80 |
| SV (hr$^{-1}$) | 0.33 | 0.33 |
| Conversion of ethanol (%) | 93.96 | 86.80 |
| Composition AEE (mol %) | 30.87 | 29.95 |
| EPE | 0.12 | 0.23 |
| EPA | 0.19 | 0.27 |
| AEE selectivity (%) | 98.63 | 97.62 |

What is claimed is:

1. A method for preparing a (meth)acrylic acid ester, which comprises reacting (meth)acrylic acid with a $C_{1-3}$ alcohol in a reactor containing a strongly acidic ion exchange resin as a catalyst, wherein the reaction is carried out under reduced pressure while the molar ratio of the alcohol to the (meth)acrylic acid is adjusted to be less than 1, wherein the reaction mixture is drawn from the reactor as a gas-liquid mixture.

2. The method according to claim 1, wherein methanol is used as the $C_{1-3}$ alcohol.

3. The method according to claim 1, wherein the molar ratio of the alcohol to the (meth)acrylic acid is from 0.3 to less than 1.

4. The method according to claim 1, wherein the reaction pressure is from 100 to 500 Torr.

5. The method according to claim 1, wherein the reaction temperature is from 60 to 130° C.

6. The method according to claim 1, wherein a fixed bed reactor is used as the reactor and the space velocity (hr$^{-1}$) of the reaction liquid supplied to the fixed bed reactor is from 0.1 to less than 1.

7. A method for preparing methyl (meth) acrylate which comprises reacting (meth)acrylic acid with methanol in a reactor containing a strongly acidic ion exchange resin as a catalyst, wherein the reaction is carried out under reduced pressure of from 100 to 500 Torr at a temperature of from 60 to 130° C. at a space velocity (hr$^{-1}$) of from 0.1 to less than 1, while the molar ratio of methanol to the (meth)acrylic acid is adjusted to be from 0.3 to less than 1, wherein the reaction mixture is drawn from the reactor as a gas-liquid mixture.

8. The method according to claim 7, wherein (meth) acrylic acid and methanol are reacted by supplying them to a fixed bed reactor packed with the strongly acidic ion exchange resin, wherein the (meth)acrylic acid and the methanol are contacted in the gas-liquid parallel flow mode.

9. The method according to claim 1, wherein a reaction mixture obtained by the reaction of (meth)acrylic acid with the alcohol under reduced-pressure, is supplied to a (meth) acrylic acid separation distillation column of a next step without cooling or condensing it.

10. The method according to claim 1, wherein a heat exchanger type multitubular reactor is used as an esterification reactor, wherein the catalyst is packed in the reaction tubes, and the reaction tubes are heated by steam or a heating medium.

11. The method according to claim 1, wherein acrylic acid is used as the (meth)acrylic acid.

* * * * *